US00PP17376P2

(12) United States Plant Patent
Kordes

(10) Patent No.: US PP17,376 P2
(45) Date of Patent: Jan. 23, 2007

(54) CLIMBING ROSE PLANT NAMED 'KORGOLGAT'

(50) Latin Name: *Rosa hybrida*
Varietal Denomination: KORgolgat

(75) Inventor: Tim-Hermann Kordes, Offenseth-Sparrieshoop (DE)

(73) Assignee: W. Kordes' Söhne Roserlachchulen GmbH & Co KG, Offenseth-Sparrieshoop (DE)

( * ) Notice: Subject to any disclaimer, the term of this patent is extended or adjusted under 35 U.S.C. 154(b) by 10 days.

(21) Appl. No.: 11/233,621

(22) Filed: Sep. 23, 2005

(51) Int. Cl.
*A01H 5/00* (2006.01)

(52) U.S. Cl. ..... Plt./111
(58) Field of Classification Search ..... Plt./111
See application file for complete search history.

*Primary Examiner*—Kent Bell
*Assistant Examiner*—June Hwu

(57) ABSTRACT

A new and distinct variety of rose with long lasting, novel golden yellow flowers, and attractive foliage with good disease resistance. It exhibits uniform, upright to climbing growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORgolgat'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1994 The crossing was between 'KORtionza', a non-patented rose by the same inventor and 'an un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORgolgat'.

SUMMARY OF THE INVENTION

The new rose plant may be distinguished from its seed parent, 'KORtionza' by the following combination of characteristics:

1. 'KORgolgat' is more vigorous than 'KORtionza', and
2. The flower of the seed parent is more yellow-orange colored.

The new rose plant may be distinguished from its pollen parent, an un-named seedling by the following combination of characteristics:

1. 'KORgolgat' is a climbing rose while the un-named seedling is a shrub, and
2. 'KORgolgat' is fragrant while the pollen parent is not.

The objective of the hybridization was to create a new and distinct rose plant with unique qualities, such as:

1. Upright, vigorous and uniform growth and flowering;
2. Abundant attractive, recurrent flowers;
3. Attractive and abundant foliage; and
3. Resistance to diseases encountered in landscapes and gardens.

This combination of qualities is not present in prior rose cultivars. These objectives have been substantially achieved and in that distinguish 'KORgolgat' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORgolgat' was selected in June 1995 from the seedling beds to be asexually propagated for further evaluation. The first asexual propagation of 'KORgolgat' was done by budding to seedling understocks in July, 1995 at the W. Kordes Söhne Nursery in Offenseth-Sparrieshoop, Germany.

This initial and other subsequent propagations conducted in controlled environments show that the foregoing and all other characteristics of 'KORgolgat' come true to form and are transmitted through succeeding generations.

BRIEF DESCRIPTION OF THE DRAWING

The accompanying color illustration shows as true as is reasonably possible to obtain in color photographs of this type, the typical characteristics of the buds, flowers, leaves, and stems of 'KORgolgat'.

Specifically illustrated in SHEET ONE are a tight bud, quarter opened bud, and fully opened flower bloom; a stem exhibiting thorns; a dissected receptacle; and a single leaf.

DETAILED BOTANICAL DESCRIPTION

The following is a description of 'KORgolgat', as observed in its growth in September, 2005 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORtionza', a non-patented rose variety from the same inventor are compared to 'KORgolgat' in Chart 1.

CHART 1

| Characteristic | 'KORgolgat' | 'KORtionza' |
|---|---|---|
| Flower bud color. | Yellow-Orange 14B. | Yellow Orange Group 17B. |
| Prickles. | Few-moderate long prickles. | Numerous small to short prickles |

Parents:
*Seed parent.*—'KORtionza'.
*Pollen parent.*—'Un-named seedling'.
Classification:
*Botanical classification.*—*Rosa hybrida,* 'KORgolgat'.
*Commercial classification.*—Climbing rose.

FLOWER AND FLOWER BUD

Blooming habit: Recurrent.
Flower bud:
*Size.*—Upon opening, 40–50 mm in length from base of receptacle to end of bud.
*Bud form.*—Pointed ovoid to high centered.
*Bud color.*—As sepals first unfold, bud color is Yellow Orange Group 14B. When ¼ open, the upper surface of petals is Yellow Orange Group 14B and the lower surface is Yellow 12B.
*Sepals.*—Size: Average 25–40 mm long×6–8 mm wide. Shape: Moderately strong foliaceous appendages on three of the five sepals. Sepal apex is cirrose. Base is flat at union with receptacle. Quantity: Five. Surface texture: Nearly smooth. Stipitate glands are present on the margins. Color: Upper surface Green Group 138B. Lower surface Green Group 138A.
Receptacle:
*Surface.*—Smooth, with a few fine white hairs.
*Color.*—Green Group 138A.
*Shape.*—Funnel.
*Size.*—7–9 mm (h)×6–8 mm (w).
Peduncle:
*Surface.*—Nearly smooth with a few fine hairs.
*Length.*—50–80 mm average length.
*Diameter.*—3 mm average diameter.
*Color.*—Green Group 138A. Some intonations of Greyed-Red Group 180B.
*Strength.*—Upright to nodding.
*Borne.*—Multiple flower buds per stem, generally 10 to 20.
Flower bloom:
*Fragrance.*—Moderate to strong spicy fragrance.
*Duration.*—On the plant 5–7 days. Senesced petals drop away.
*Size.*—Medium to large flowered garden rose. Average flower diameter is 80 mm when open.
*Form.*—Shape of flower when viewed from the side: Upon opening, upper part: Flattened convex. Upon opening, lower part: Flat. Open flower, upper part: Flattened convex. Open flower, lower part: Flat.
Color:
*Upon opening, petals.*—Outermost petals: Outer Side: Upper half of petal Yellow Group 12B. Lower half of petal Yellow Group 13C. Inner Side: Yellow Group 13C. Innermost petals: Outer Side: Yellow Orange Group 14B. Inner Side: Yellow Orange Group 14B.
*Upon opening, basal petal spot.*—No distinctive coloration at petal base.
*After opening, petals.*—Outermost petals: Outer Side: Yellow Group 12B. Inner Side: Yellow Group 12A. Innermost petals: Outer Side: Yellow Group 12B. Inner Side: Yellow Group 12A.
*Upon opening, basal petal spot.*—No distinctive coloration at petal base.
*Variegations.*—None observed.
General tonality: On open flower Yellow Orange Group 14B. No change in the general tonality at the end of the third day. Afterwards, general tonality is Yellow Group 12B.
Petals:
*Petal count.*—Approximately 55–60 petals under normal conditions.
*Petal reflex.*—Some petals reflex slightly.
*Petal edge.*—Variable. Entire to ruffled.
*Petal shape.*—Apex shape is round. Shape of base is attenuate. Many petals and petaloids are long and narrow at the point of attachment.
*Petal size.*—35–45 mm long; 25–35 mm wide.
*Thickness.*—Average.
*Petal arrangement.*—Informal.
*Petaloids.*—Present. Numerous. Average of 20–30 per flower. Petaloids are 12–15 mm long and 10 mm wide. Color of inner side is Yellow Orange Group 14B. Color of outer side is Yellow Orange Group 14B. Surface texture is smooth. Shape is variable, linear to elliptic.
Reproductive organs:
*Pistils.*—Abundant. Approximately 45–55 present. Stigmas: Location: At the same position as the anthers. Color: Greyed-Red Group 180B. Styles: Length: 15 mm long. Color: Green-Yellow Group 1C. Intonations of Greyed-Red Group 180B below stigma.
*Stamens.*—Average 55 in number. Anthers: Size: 2 mm long. Color: Yellow Orange Group 17B. Quantity: Approximately 50–60. Pollen: Not observed. Filaments: Color: Yellow Orange Group 14B. Length: 10–15 mm. Quantity: Approximately 50–60.

THE PLANT

Plant growth: Vigorous. Upright to climbing habit. When grown as a budded nursery plant the average plant height is 2.5 m and the average plant width is 100 cm.
Stems:
*Stem color.*—Young wood: Green Group 138A. Older wood: Green Group 138A.
*Stem surface.*—Young wood: Smooth. Older wood: Smooth.
Prickles: Present.
*Incidence.*—5–6 per 10 cm of stem.
*Size.*—Moderately large. Average length: 10–12 mm. Some to 15 mm.
*Color.*—Greyed-Red Group 178B. With age, turning Brown Group 200C.
*Shape.*—On upper stems, linear to slightly downward hooked. On lower stems, deeply concave.

Leaves and leaflets: Normally 5–7 leaflets on normal leaves in middle of the stem.

*Leaf size.*—Average 150 mm (l)×110 mm (w). Some leaves to 180 mm long and 130 mm wide.

*Quantity.*—Average to abundant.

*Texture.*—Semi glossy. Leathery.

*Color, mature foliage.*—Upper Leaf Surface: Green Group 138A. Lower Leaf Surface: Green Group 138B.

*Color, juvenile foliage.*—Upper Leaf Surface: Green Group 138A. Lower Leaf Surface: Green Group 138B.

*Anthocyanin intonation.*—Present on margins and underneath leaflets. Greyed-Red Group 183C.

Stipules:

*Size.*—15 mm (l)–4–5 mm (w).

*Stipule color.*—Green Group 138A.

*Presence of stipitate glands.*—Variable. Some leaflet margins with few to none. Others have abundant stipulate glands.

*Margins.*—Serrated.

Petiole:

*Length.*—5–20 mm.

*Diameter.*—4–5 mm.

*Petiole color.*—Green Group 138A. Anthocyanin present on juvenile tissue. Greyed-Red Group 183C. Margins generally with anthocyanin.

*Prickles.*—A few small prickles underneath.

*Stipitate glands.*—Generally lacking.

Petiole rachis:

*Length.*—5–20 mm.

*Diameter.*—4–5 mm.

*Petiole color.*—Green Group 138A. Anthocyanin present on juvenile tissue. Greyed-Red Group 183C. Margins generally with anthocyanin.

*Prickles.*—A few small prickles underneath.

*Stipitate glands.*—Generally lacking.

Leaflets:

*Size.*—Average size of the terminal leaflet is 60 mm(l)× 45 mm(w).

*Shape.*—Pointed oval.

*Margins.*—Finely serrated.

*Texture.*—Leathery.

Hips/seed formation: Large hips observed. Width: 22 mm. Height: 18 mm. Color: Green Group 146C. Changing to Greyed-Orange 169D.

Winter hardiness: To date, the variety has been grown successfully in Zone 5.

Disease resistance: Above average resistance to disease under normal growing conditions.

I claim:

1. A new and distinct variety of rose plant characterized by the following combination of characteristics:

(a) forms attractive, long lasting golden yellow flowers;

(b) exhibits uniform upright to climbing growth habit;

(c) propagates well using traditional methods, and;

(d) exhibits very good resistance to disease under normal growing conditions;

substantially as herein illustrated and described.

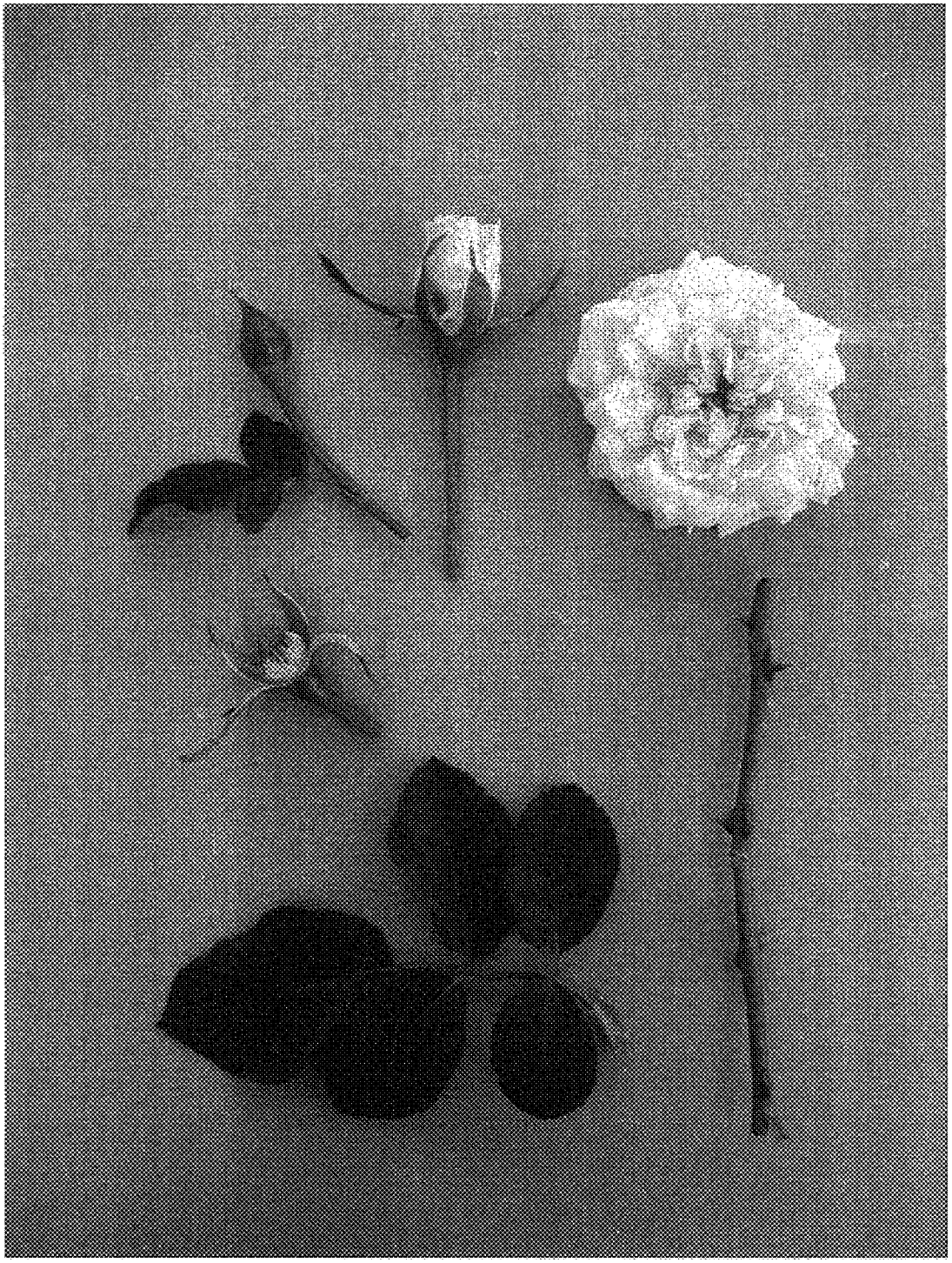

* * * * *